US00RE48889E

(19) United States
(12) Reissued Patent
Peng et al.

(10) Patent Number: US RE48,889 E
(45) Date of Reissued Patent: Jan. 11, 2022

(54) DEHYDROFLUORINATION OF 245FA TO 1234ZE

(71) Applicant: THE CHEMOURS COMPANY FC, LLC, Wilmington, DE (US)

(72) Inventors: Sheng Peng, Hockessin, DE (US); Mario Joseph Nappa, Leesburg, FL (US)

(73) Assignee: THE CHEMOURS COMPANY FC, LLC, Wilmington, DE (US)

(21) Appl. No.: 16/193,924

(22) Filed: Nov. 16, 2018

Related U.S. Patent Documents

Reissue of:
(64) Patent No.: 9,302,962
Issued: Apr. 5, 2016
Appl. No.: 14/819,807
Filed: Aug. 6, 2015

U.S. Applications:
(60) Provisional application No. 62/037,138, filed on Aug. 14, 2014.

(51) Int. Cl.
*C07C 17/25* (2006.01)

(52) U.S. Cl.
CPC ..... *C07C 17/25* (2013.01)

(58) Field of Classification Search
CPC ..... C07C 17/25
See application file for complete search history.

(56) References Cited

U.S. PATENT DOCUMENTS

| | | | | |
|---|---|---|---|---|
| 3,413,363 | A | 11/1968 | Pindzola | |
| 5,811,603 | A | 9/1998 | Elsheikh | |
| 5,986,151 | A | 11/1999 | Van Der Puy | |
| 6,023,004 | A | 2/2000 | Thenappan et al. | |
| 6,034,289 | A | 3/2000 | Christoph et al. | |
| 6,124,510 | A | 9/2000 | Elsheikh et al. | |
| 6,548,719 | B1 | 4/2003 | Nair et al. | |
| 7,189,884 | B2 | 3/2007 | Mukhopadhyay et al. | |
| 7,230,146 | B2 | 6/2007 | Merkel et al. | |
| 7,345,209 | B2 | 3/2008 | Mukhopadhyay et al. | |
| 7,485,760 | B2 | 2/2009 | Wang et al. | |
| 7,563,384 | B2 | 7/2009 | Thomas et al. | |
| 7,563,936 | B2 | 7/2009 | Wang et al. | |
| 7,592,494 | B2 | 9/2009 | Tung et al. | |
| 7,638,660 | B2 | 12/2009 | Wang et al. | |
| 7,674,939 | B2 | 3/2010 | Mukhopadhyay et al. | |
| 7,714,177 | B2 | 5/2010 | Mukhopadhyay et al. | |
| 7,803,973 | B2 | 9/2010 | Merkel et al. | |
| 7,829,748 | B1 | 11/2010 | Tung et al. | |
| 7,880,040 | B2 | 2/2011 | Mukhopadhyay et al. | |
| 7,897,823 | B2 | 3/2011 | Miller et al. | |
| 7,973,202 | B2 | 7/2011 | Takahashi et al. | |
| 8,067,650 | B2 | 11/2011 | Wang et al. | |
| 8,115,037 | B2 | 2/2012 | Sakyu et al. | |
| 8,247,624 | B2 | 8/2012 | Merkel et al. | |
| 8,338,651 | B2 | 12/2012 | Uenveren et al. | |
| 8,426,656 | B2 | 4/2013 | Merkel et al. | |
| 8,436,217 | B2 | 5/2013 | Wang et al. | |
| 8,513,473 | B2 | 8/2013 | Sakyu et al. | |
| 8,518,293 | B2 | 8/2013 | Hulse et al. | |
| 8,546,623 | B2 | 10/2013 | Sharratt et al. | |
| 9,187,386 | B2 * | 11/2015 | Sun | C07C 17/25 |
| 9,255,046 | B2 | 2/2016 | Cottrell et al. | |
| 9,334,207 | B2 | 5/2016 | Pokrovski et al. | |
| 9,359,274 | B2 | 6/2016 | Yoshikawa et al. | |
| 9,428,430 | B2 * | 8/2016 | Fukushima | C07C 21/18 |
| 9,492,816 | B2 | 11/2016 | Elsheikh et al. | |
| 9,771,309 | B2 | 9/2017 | Sharratt et al. | |
| 10,029,963 | B2 | 7/2018 | Bonnet et al. | |
| 10,227,275 | B2 | 3/2019 | Pigamo et al. | |
| 2007/0100173 | A1 * | 5/2007 | Miller | C01B 7/191 570/178 |
| 2007/0129579 | A1 | 6/2007 | Wang et al. | |
| 2007/0179324 | A1 | 8/2007 | Van Der Puy et al. | |
| 2008/0051610 | A1 * | 2/2008 | Wang | C01B 7/191 570/156 |

(Continued)

FOREIGN PATENT DOCUMENTS

| | | | |
|---|---|---|---|
| CN | 1261337 | A | 7/2000 |
| CN | 100473633 | C | 4/2009 |

(Continued)

OTHER PUBLICATIONS

Honeywell brochure entitled "SolsticeTM ze (HFO-1234ze) Refrigerant". (Year: 2012).*

Gas Chromatography: Calculating the Area (http://faculty.sdmiramar.edu/fgarces/LabMatters/ChemTech/modules/gaschrom/gaschromcalc.htm (Year: 2021).*

Communication of a notice of opposition dated Sep. 20, 2019 for EP Counterpart Patent No. 3180299 (Application No. 15750575.1).

Submission of Opposition by Arkema France dated Sep. 17, 2019 for EP Counterpart Patent No. 3180299 (Application No. 15750575.1).

Lenher, Samual, "The Reaction between Oxygen and Propylene: Activation, Oxidation and Polymerization," Published May 7, 1932, vol. 54, pp. 1830-1837.

Mass Flow versus Volumetric Flow and Flow Rate Unit Conversions, Sensing and Control, Honeywell, Technical Note, Nov. 2012, pp. 1-4.

Apr. 15, 2020 Response to Official Communication dated Oct. 4, 2019.

Jul. 7, 2020 EPO Summons to Attend Oral Proceedings.

Jan. 8, 2021 EPO Filing in Preparation of the Oral Hearing.

Apr. 16, 2021 EPO Decision rejecting the opposition.

*Primary Examiner* — Alan D Diamond

(57) ABSTRACT

A method of producing a [fluoropropane] *fluoropropene* of formula $CF_3CH{=}CHF$, comprising contacting a mixture of 1,1,1,3,3-pentafluoropropane and Z-1,3,3,3-tetrafluoropropene in the gas phase with a catalyst comprising at least one catalyst selected from the group consisting of fluorinated $Cr_2O_3$ or Cr/Ni on fluoride alumina, in the presence of an oxygen containing gas, to form a mixture comprising [Z-1,3,3,3-tetrafluoropropane] *Z-1,3,3,3-tetrafluoropropene*, E-1,3,3,3,-tetrafluoropropene, hydrogen fluoride, and optionally unreacted 1,1,1,3,3-pentafluoropropane, separating the E-1,3,3,3-tetrafluoropropene from the Z-isomer and any unreacted 1,1,1,3,3-pentafluoropropane, if present, and recovering said E-1,3,3,3-tetrafluoropropene.

23 Claims, No Drawings

(56) References Cited

U.S. PATENT DOCUMENTS

| | | | | |
|---|---|---|---|---|
| 2010/0022809 | A1 | 1/2010 | Cottrell et al. | |
| 2010/0185027 | A1 | 7/2010 | Wang et al. | |
| 2011/0152585 | A1 | 6/2011 | Takahashi et al. | |
| 2011/0172472 | A1 | 7/2011 | Sakyu et al. | |
| 2011/0319674 | A1 | 12/2011 | Wang et al. | |
| 2012/0056122 | A1 | 3/2012 | Hulse et al. | |
| 2012/0059200 | A1* | 3/2012 | Pokrovski | C01B 7/0706 570/156 |
| 2012/0065435 | A1 | 3/2012 | Nishiguchi et al. | |
| 2012/0184786 | A1 | 7/2012 | Merkel et al. | |
| 2013/0211155 | A1 | 8/2013 | Nair et al. | |
| 2013/0261353 | A1 | 10/2013 | Pokrovski et al. | |
| 2015/0307420 | A1* | 10/2015 | Xu | C07C 17/25 570/157 |

FOREIGN PATENT DOCUMENTS

| | | | |
|---|---|---|---|
| CN | 1976885 | B | 5/2010 |
| CN | 1902152 | B | 10/2010 |
| CN | 1852880 | B | 6/2011 |
| CN | 102513136 | B | 11/2011 |
| CN | 101175564 | B | 9/2012 |
| CN | 101517031 | B | 4/2013 |
| CN | 101522597 | B | 5/2013 |
| CN | 101466656 | B | 7/2013 |
| CN | 101821220 | B | 8/2013 |
| CN | 102105422 | B | 10/2013 |
| CN | 101801894 | B | 6/2014 |
| CN | 101868436 | B | 7/2014 |
| CN | 101260021 | B | 8/2014 |
| CN | 102112421 | B | 11/2014 |
| CN | 104159877 | A | 11/2014 |
| CN | 102282114 | B | 12/2014 |
| CN | 104185616 | A | 12/2014 |
| CN | 101214446 | B | 2/2015 |
| CN | 102918010 | B | 2/2015 |
| CN | 103153924 | B | 4/2015 |
| CN | 102164881 | B | 5/2015 |
| CN | 103537305 | B | 5/2015 |
| CN | 104789193 | A | 7/2015 |
| CN | 103143344 | B | 10/2015 |
| CN | 102164882 | B | 11/2015 |
| CN | 103038198 | B | 11/2015 |
| CN | 105050991 | A | 11/2015 |
| CN | 103476736 | B | 2/2016 |
| CN | 105727929 | A | 7/2016 |
| CN | 103097325 | B | 10/2016 |
| CN | 104411667 | B | 11/2016 |
| CN | 106660909 | A | 5/2017 |
| CN | 106831316 | A | 6/2017 |
| CN | 106883095 | A | 6/2017 |
| CN | 105037077 | B | 12/2017 |
| CN | 107892642 | A | 4/2018 |
| EP | 0486333 | A1 | 5/1992 |
| EP | 1 900 716 | A1 | 3/2008 |
| JP | 11-140002 | A | 5/1999 |
| WO | 2008/008350 | A2 | 1/2008 |
| WO | 2008/147835 | A1 | 12/2008 |
| WO | 2009/003157 | A1 | 12/2008 |
| WO | 2010/021406 | A1 | 2/2010 |
| WO | 2013/164618 | A1 | 11/2013 |

* cited by examiner

DEHYDROFLUORINATION OF 245FA TO 1234ZE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE TO RELATED APPLICATIONS*

*This application is a Reissue of U.S. Pat. No. 9,302,962 B2 issued Apr. 5, 2016 that claims priority to U.S. Provisional Application No. 62/037,138, filed Aug. 14, 2014.*

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

HFC-1234yf ($CF_3CF{=}CH_2$) and HFC-1234ze ($CF_3CH{=}CHF$), both having zero ozone depletion and low global warming potential, have been identified as potential refrigerants. U.S. Patent Publication No. 2006/0106263 A1 discloses the production of HFC-1234yf by a catalytic vapor phase dehydrofluorination of $CF_3CF_2CH_3$ or $CF_3CHFCH_2F$, and of HFC-1234ze (mixture of E- and Z-isomers) by a catalytic vapor phase dehydrofluorination of $CF_3CH_2CHF_2$.

The catalytic dehydrofluorination of hydrofluorocarbons to produce hydrofluoroolefins is ordinarily carried out in the vapor phase using a dehydrofluorination catalyst. Vapor phase dehydrofluorination catalysts are well known in the art. These catalysts include, but are not limited to, alumina, aluminum fluoride, fluorided alumina, metal compounds on aluminum fluoride, metal compounds on fluorided alumina; chromium oxides, fluorided chromium oxides, and cubic chromium trifluoride; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. In the alternative, dehydrofluorinations can be carried out in the liquid phase through reaction with aqueous or alcohol solutions of caustic, such as potassium hydroxide, or sodium hydroxide.

Catalytic dehydrofluorination of HFC-245fa in general produces a mixture of both the E-isomer as well as the Z-isomer of HFC-1234ze. Depending on the particular catalyst chosen, the amount of the Z-isomer can vary between 15 to 23%. Dehydrofluorination in the liquid phase using aqueous solutions of caustic or other strong bases also produces mixture of both isomers. Although the ratio of the two isomers can be shifted somewhat by temperature, about 13-15% of the Z-isomer is typically formed. As the E-isomer is the most useful for refrigeration applications, after separation of the E-isomer from the Z-isomer, the Z-isomer is typically either isomerized to the E-isomer in a separate step, or converted back to 245fa through addition of hydrogen fluoride. Both alternatives require additional steps which add cost.

There is a continuing need for more selective and efficient manufacturing processes for the production of HFC-1234ze and HFC-1234yf.

SUMMARY

Described is a method of producing a [fluoropropane] *fluoropropene* of formula $CF_3CH{=}CHF$, comprising contacting a mixture of 1,1,1,3,3-pentafluoropropane and Z-,1,3,3,3-tetrafluoropropene in the gas phase with a catalyst comprising at least one catalyst selected from the group consisting of fluorinated $Cr_2O_3$ or Cr/Ni on fluorided alumina, optionally in the presence of an oxygen containing gas, to form a mixture comprising [Z-1,3,3,3-tetrafluoropropane] *Z-1,3,3,3-tetrafluoropropene*, E-1,3,3,3,-tetrafluoropropene, and optionally unreacted 1,1,1,3,3-pentafluoropropane, separating the E-1,3,3,3-tetrafluoropropene from the Z-isomer and any unreacted 1,1,1,3,3-pentafluoropropane, if present, and returning said Z-1,3,3,3-tetrafluoropropene to be fed to the reactor with additional 1,1,1,3,3-pentafluoropropane.

The foregoing general description and the following detailed description are exemplary and explanatory only and are not restrictive of the invention, as defined in the appended claims.

DETAILED DESCRIPTION

Described is a method of producing a [fluoropropane] *fluoropropene* of formula $CF_3CH{=}CHF$, comprising contacting a mixture of 1,1,1,3,3-pentafluoropropane and Z-,1,3,3,3-tetrafluoropropene in the gas phase with a catalyst comprising at least one catalyst selected from the group consisting of fluorinated $Cr_2O_3$ or Cr/Ni on fluoride alumina, optionally in the presence of an oxygen containing gas, to form a mixture comprising [Z-1,3,3,3-tetrafluoropropane] *Z-1,3,3,3-tetrafluoropropene*, E-1,3,3,3,-tetrafluoropropene, and optionally unreacted 1,1,1,3,3-pentafluoropropane, separating the E-1,3,3,3-tetrafluoropropene from the Z-isomer and any unreacted 1,1,1,3,3-pentafluoropropane, if present, and returning said Z-1,3,3,3-tetrafluoropropene to be fed to the reactor with additional 1,1,1,3,3-pentafluoropropane.

Dehydrofluorination reactions are well known in the art. The dehydrofluorination of HFC-245fa has been particularly studied. Both gas phase and liquid phases processes are known. 1,3,3,3-Tetrafluoropropene (HFO-1234ze) exists as both a Z-isomer and an E-isomer about the double bond. Both gas phase and liquid phase processes are known to produce a mixture of both the Z- and E-isomers, with the E-isomer predominating. The selectivity for the production of the Z-isomer can vary from about 10% to about 23%, depending on the temperature, and choice of catalyst. The boiling point of the E-isomer at 1 atm is about −19 C, while the boiling point of the Z-isomer is about +9 C. For many uses, the E-isomer is preferred. So as to minimize yield losses in the form of the generally unwanted Z-isomer, it becomes necessary to either add an isomerization step to isomerize the Z-isomer to the E-isomer, or add a fluorination step to convert Z-1234ze back to HFC-245fa.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

Dehydrofluorinations are known in the art, and are preferably conducted in the vapor phase. The dehydrofluorination reaction may be conducted in any suitable reaction vessel or reactor, but it should preferably be constructed from materials which are resistant to the corrosive effects of hydrogen fluoride, such as nickel and it's alloys, including Hastelloy, Monel, and Inconel, or vessels lined with fluoropolymers. These may be a single tube, or multiple tubes packed with a dehydrofluorination catalyst.

Useful catalysts for the process include chromium-based catalysts such as fluorided chromium oxide, which catalyst may either be unsupported, or supported on a support such as activated carbon, graphite, fluoride graphite, or fluorided alumina. The chromium catalyst may either be used alone, or in the presence of a co-catalyst selected from nickel, cobalt, manganese or zinc salt. In one embodiment, a chromium catalyst is high surface area chromium oxide, or chromium/nickel on fluoride alumina ($Cr/Ni/AlF_3$), the preparation of which is reported in European Patent EP 486,333. In another embodiment, the catalyst is fluorided Guignet's green catalyst. The chromium catalysts are preferably activated before use, typically by a procedure whereby the catalyst is heated to from 350 to 400° C. under a flow of nitrogen for a period of time, after which the catalyst is heated under a flow of HF and nitrogen or air for an additional period of time.

In one embodiment, the Guignet's Green of the fluoride-activated Guignet's Green catalyst used in the present invention is made by reacting (fusing) boric acid with alkali metal dichromate at 500° C. to 800° C., followed by hydrolysis of the reaction product, whereby said Guignet's Green contains boron, alkali metal, and water of hydration. The usual alkali metal dichromates are the Na and/or K dichromates. The reaction is typically followed by the steps of cooling the reaction product in air, crushing this solid to produce a powder, followed by hydrolysis, filtering, drying, milling and screening. The Guignet's Green is bluish green, but is known primarily as a green pigment, whereby the pigment is commonly referred to as Guignet's Green. When used as a catalyst, it is also referred to as Guignet's Green as disclosed in U.S. Pat. No. 3,413,363. In U.S. Pat. No. 6,034,289, $Cr_2O_3$ catalysts are disclosed as preferably being in the alpha form, and Guignet's Green is also disclosed as a commercially available green pigment having the composition: $Cr_2O_3$ 79-83%, $H_2O$ 16-18 wt %, $B_2O_5$ 1.5 to 2.7% (sentence bridging cols. 2 and 3) that can be converted to the alpha form (col. 3, I. 3). U.S. Pat. No. 7,985,884 acknowledges the presence of alkali metal in the Guignet's Green in the composition of Guignet's Green disclosed in Example 1: 54.5% Cr, 1.43% B, 3400 ppm Na, and 120 ppm K.

The physical shape of the catalyst is not critical and may, for example, include pellets, extrudates, powders, or granules. The fluoride activation of the catalyst is preferably carried out on the final shape of the catalyst.

In one embodiment, the current inventors have discovered that feeding a mixture of HFC-245fa and at least about 10% by weight of the Z-isomer of HFO-1234ze to a dehydrofluorination reactor in the presence of an oxygen containing gas can suppress the formation of additional Z-isomer so that the HFC-245fa converted by dehydrofluorination produces substantially only E-HFO-1234ze. Feeding less than about 10% will result in some suppression of the formation of additional Z-1234ze. Feeding greater than about 10% by weight of Z-1234ze simply results in the presence of additional material which must be separated and recycled. The amount of Z-1234ze which is necessary to suppress the further formation of Z-isomer product is dependent to some extent on conversion. At 70% conversion of 245fa, about 10-11% Z-isomer in the feed is required. At 80% conversion, about 13% Z-isomer in the feed is required.

In one embodiment, the reaction vessel can be held at a temperature of between 200° C. and 375° C. In another embodiment, the reaction vessel can be held at a temperature of between 250° C. and 350° C. In yet another embodiment, the reaction vessel can be held at a temperature of between 275° C. and 325° C.

The reaction pressure can be subatmpospheric, atmospheric or superatmostpheric. In one embodiment, the reaction is conducted at a pressure of from 14 psig to about 100 psig. In another embodiment, the reaction is conducted at a pressure of from 14 psig to about 60 psig. In yet another embodiment, the reaction is conducted at a pressure of from 40 psig to about 85 psig. In yet another embodiment, the reaction is conducted at a pressure of from 50 psig to 75 psig. In general, increasing the pressure in the reactor above atmospheric pressure will act to increase the contact time of the reactants in the process. Longer contact times will necessarily increase the degree of conversion in a process, without having to increase temperature.

Depending on the temperature of the reactor, and the contact time, the product mixture from the reactor will contain varying amounts of unreacted HFC-245fa. E-1,3,3,3-tetrafluoropropene is then separated from the Z-1,3,3,3-tetrafluoropropene, hydrogen fluoride, and any unreacted HFC-245fa, which are then recycled back to the reactor with additional HFC-245fa. Hydrogen fluoride may be removed by scrubbing, by passing the reactor effluent through a solution of aqueous caustic, or hydrogen fluoride may be removed by distillation.

In one embodiment, the reactor feed is preheated in a vaporizer to a temperature of from about 30° C. to about 100° C. In another embodiment, the reactor feed is preheated in a vaporizer to a temperature of from about 30° C. to about 80° C.

In some embodiments, an inert diluent gas is used as a carrier gas for the hydrochlorofluoropropane. In one embodiment, the carrier gas is selected from nitrogen, argon, helium or carbon dioxide.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The transitional phrase "consisting of" excludes any element, step, or ingredient not specified. If in the claim, such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" is used to define a composition, method that includes materials, steps, features, components, or elements, in addition to those literally disclosed provided that these additional included materials, steps, features, components, or elements do not materially affect the basic and novel characteristic(s) of the claimed invention, especially the mode of action to achieve the desired result of any of the processes of the present invention. The term 'consisting essentially of' occupies a middle ground between "comprising" and 'consisting of'.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is citedIn case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

Example 1

Example 1 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Johnson Mathey) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 1.

TABLE 1

| % Z-ze added | 0 | 7.5 | 10.9 |
|---|---|---|---|
| Incoming compos | 100/0 | 92.5/7.5 | 89/11 |
| 245fa conversion (%) | 71.2 | 69.3 | 72 |
| Z-ze in product (%) | 10.7 | 10.3 | 11.2 |
| % recovered 245fa | 28.8 | 28.4 | 24.9 |
| % E-ze | 60.5 | 60.3 | 63.9 |
| % yield E-ze | 60.5 | 65.3 | 71.7 |
| % selectivity E-ze | 85 | 94.2 | 99.7 |

Example 2

Example 2 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Guignet's green) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 2.

TABLE 2

| % Z-ze added | 0 | 10.9 |
|---|---|---|
| Incoming compos | 100/0 | 89/11 |
| 245fa conversion (%) | 69.9 | 71.8 |
| Z-ze in product (%) | 10.7 | 10.9 |
| % recovered 245fa | 30.1 | 25.1 |
| % E-ze | 59.2 | 64 |
| % yield E-ze | 59.2 | 71.9 |
| % selectivity E-ze | 84.7 | 100 |

Example 3

Example 3 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Johnson Mathey) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 3.

TABLE 3

| % Z-ze added | 0 | 10.9 |
|---|---|---|
| Incoming compos | 100/0 | 89/11 |
| 245fa conversion (%) | 73 | 71.3 |
| Z-ze in product (%) | 11.4 | 11.0 |
| % recovered 245fa | 27.0 | 25.5 |
| % E-ze | 61.6 | 63.5 |
| % yield E-ze | 61.6 | 72.5 |
| % selectivity E-ze | 84 | 100 |

Example 4

Example 4 demonstrates the dehydrofluorination of 245fa over $Cr_2O_3$ in the presence of Z-HFC-1234ze.

An inconel tube (½ inch OD) was filled with 10 cc (8 gm) of $Cr_2O_3$ catalyst (Newport Cr) which had been prepared as follows. Chromic oxide in extrudate form, which was crushed and sieved to 12/20 mesh. After charging the reactor tube, the temperature of the catalyst bed was raised to 300° C. and purged with nitrogen (30 cc/min) for 200 minutes. Then the flow of nitrogen was reduced to 60 cc/min and HF was fed at 20 cc/min for 60 minutes. The temperature was increase to 325° C. for 300 minutes. The flow of nitrogen was then lowered to 30 cc/min and the flow of HF was raised to 30 cc/min for 30 minutes. The flow of nitrogen was then lowered to 12 cc/min and the flow of HF was raised to 48 cc/min for 60 minutes. The flow of nitrogen was then discontinued and the flow of HF was raised to 48 cc/min for 30 minutes. The reactor temperature was then decreased to 250° C. for 30 minutes. Afterwards HF was turned off and the reactor was purged with 30 cc/min of nitrogen. The reactor temperature was then stabilized at 300° C., the flow of nitrogen was turned off, and either $CF_3CH_2CHF_2$, or $CF_3CH_2CHF_2$ with varying amounts of Z-1234ze, was fed at 1.44 ml/hr. Contact time in the reactor was 45 seconds. The $CF_3CH_2CHF_2$ was vaporized at 50° C. Part of the reactor effluent was passed through a series of valves and analyzed by GCMS. Amounts for Z-1234ze, 245fa and E-1234ze are expressed as mole percent. Results are summarized in Table 4.

TABLE 4

| % Z-ze added | 0 | 10.7 |
|---|---|---|
| Incoming compos | 100/0 | 89.3/10.7 |
| 245fa conversion (%) | 72.2 | 70.2 |
| Z-ze in product (%) | 10.4 | 10.5 |
| % recovered 245fa | 27.8 | 26.6 |
| % E-ze | 61.8 | 62.9 |
| % yield E-ze | 61.8 | 70.4 |
| % selectivity E-ze | 85.5 | 100 |

Example 5

Example 4 demonstrates the dehydrofluorination of 245fa over fluorided alumina in the presence of Z-HFC-1234ze.

An inconel tube (½ inch OD) is filled with 10 cc (6.1 gm) of Al2O3 catalyst (purchased from Sigma-Aldrich). Al2O3 in extrudate form, which is crushed and sieved to 12/20 mesh. After charging the reactor tube, the temperature of the catalyst bed is raised to 300° C. and purged with nitrogen (30 cc/min) for 200 minutes. Then the flow of nitrogen is reduced to 60 cc/min and HF is fed at 20 cc/min for 60 minutes. The temperature is increase to 325° C. for 300 minutes. The flow of nitrogen is then lowered to 30 cc/min and the flow of HF is raised to 30 cc/min for 30 minutes. The flow of nitrogen is then lowered to 12 cc/min and the flow of HF is raised to 48 cc/min for 60 minutes. The flow of nitrogen is then discontinued and the flow of HF is raised to 48 cc/min for 30 minutes. The reactor temperature is then decreased to 250° C. for 30 minutes. Afterwards HF is turned off and the reactor is purged with 30 cc/min of nitrogen. The reactor temperature is then stabilized at 300° C., the flow of nitrogen is turned off, and either $CF_3CH_2CHF_2$, or $CF_3CH_2CHF_2$ with varying amounts of Z-1234ze, is fed at 1.44 ml/hr. Contact time in the reactor is 45 seconds. The $CF_3CH_2CHF_2$ is vaporized at 50° C. Part of the reactor effluent is passed through a series of valves and analyzed by GCMS. Amounts for Z-1234ze, 245fa and E-1234ze are expressed as mole percent. Results are summarized in Table 5.

TABLE 5

| % Z-ze added | 0 | 10.9 |
|---|---|---|
| Incoming compos | 100/0 | 89/11 |
| 245fa conversion (%) | 70 | 71 |
| Z-ze in product (%) | 11 | 11 |
| % recovered 245fa | 30 | 29 |

TABLE 5-continued

| % Z-ze added | 0 | 10.9 |
|---|---|---|
| % E-ze | 59 | 58 |
| % yield E-ze | 59 | 65 |
| % selectivity E-ze | 84.3 | 100 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A method of producing a [fluoropropane] *fluoropropene* of formula $CF_3CH{=}CHF$ *while suppressing additional production of Z-1,3,3,3-tetrafluoropropene*, comprising: a) *providing and* contacting a *starting feed* mixture of 1,1,1,3,3-pentafluoropropane and *at least 10% by weight* Z-1,3,3,3-tetrafluoropropene *to suppress its production* in the gas phase with a catalyst comprising at least one catalyst selected from the group consisting of fluorinated $Cr_2O_3$ or Cr/Ni on fluorided alumina, in the presence of an oxygen containing gas, to form a *product* mixture comprising [Z-1,3,3,3-tetrafluoropropane] *Z-1,3,3,3-tetrafluoropropene*, E-1,3,3,3[,]-tetrafluoropropene, hydrogen fluoride, and [optionally] unreacted 1,1,1,3,3-pentafluoropropane, b) separating the E-1,3,3,3-tetrafluoropropene from the Z-isomer and [any] unreacted 1,1,1,3,3-pentafluoropropane, [if present,] and c) recovering said E-1,3,3,3-tetrafluoropropene.

[2. The method of claim 1, wherein said mixture of 1,1,1,3,3-pentafluoropropane and Z-1,3,3,3-tetrafluoropropene comprises at least 7% by weight Z-1,3,3,3-tetrafluoropropene.]

[3. The method of claim 1, wherein said mixture of 1,1,1,3,3-pentafluoropropane and Z-1,3,3,3-tetrafluoropropene comprises at least 10% by weight Z-1,3,3,3-tetrafluoropropene.]

4. The method of claim 1, wherein [at least 94%] *the isomeric selectivity of the conversion* of the 1,1,1,3,3-pentafluoropropane [is converted] to E-isomer of [1,3,3,3-tetrafloropropene] *1,3,3,3-tetrafluoropropene is at least 94 mol* %.

5. The method of claim 1, wherein [at least 98%] *the isomeric selectivity of the conversion* of the 1,1,1,3,3-pentafluoropropane [is converted] to E-isomer of [1,3,3,3-tetrafloropropene] *1,3,3,3-tetrafluoropropene is at least 98 mol* %.

6. The method of claim 1, further comprising recovering Z-1,3,3,3-tetrafluoropropene, or a mixture of Z-1,3,3,3-tetrafluoropropene and 1,1,1,3,3-pentafluoropropane, and recycling Z-1,3,3,3-tetrafluoropropene, or a mixture of Z-1,3,3,3-tetrafluoropropene and 1,1,1,3,3-pentafluoropropane back to step a).

7. The [process] *method* of claim 1, wherein said hydrogen fluoride produced in step a) is separated and recovered.

8. The [process] *method* of [step] *claim* 1, wherein said oxygen containing gas is oxygen, or air.

*9. The method of claim 8, wherein said oxygen containing gas is oxygen.*

*10. The method of claim 9, further providing the E-1,3,3,3-tetrafluoropropene to a refrigerant system.*

*11. A method comprising: a) contacting a starting feed mixture of 1,1,1,3,3-pentafluoropropane and at least 10% by weight Z-1,3,3,3-tetrafluoropropene in the gas phase with a catalyst comprising at least one catalyst selected from the group consisting of fluorinated $Cr_2O_3$ or Cr/Ni on fluorided alumina, in the presence of an oxygen containing gas in a reactor, to suppress additional formation of the Z-1,3,3,3-tetrafluoropropene and form a reactor product mixture comprising Z-1,3,3,3-tetrafluoropropene, E-1,3,3,3-tetrafluoropropene, hydrogen fluoride, and optionally unreacted 1,1,1,3,3-pentafluoropropane, b) separating the E-1,3,3,3-tetrafluoropropene from the Z-isomer and any unreacted 1,1,1,3,3-pentafluoropropane, if present, and c) recovering said E-1,3,3,3-tetrafluoropropene and providing the E-1,3,3,3-tetrafluoropropene to a refrigerant system.*

*12. The method of claim 11, the method including operating the refrigerant system, wherein the refrigerant system comprises the E-1,3,3,3-tetrafluoropropene.*

*13. The method of claim 1, wherein said mixture of 1,1,1,3,3-pentafluoropropane and Z-1,3,3,3-tetrafluoropropene comprises at least 11% by weight Z-1,3,3,3-tetrafluoropropene.*

*14. The method of claim 12, wherein the isomeric selectivity of the conversion of the 1,1,1,3,3-pentafluoropropane to E-isomer of 1,3,3,3-tetrafluoropropene is at least 94 mol* %.

*15. The method of claim 12, wherein the isomeric selectivity of the conversion of the 1,1,1,3,3-pentafluoropropane to E-isomer of 1,3,3,3-tetrafluoropropene is at least 98 mol* %.

*16. The method of claim 12, further comprising recovering Z-1,3,3,3-tetrafluoropropene, or a mixture of Z-1,3,3,3-tetrafluoropropene and 1,1,1,3,3-pentafluoropropane, and recycling Z-1,3,3,3-tetrafluoropropene, or a mixture of Z-1,3,3,3-tetrafluoropropene and 1,1,1,3,3-pentafluoropropane back to step a).*

*17. The process of claim 12, wherein said hydrogen fluoride produced in step a) is separated and recovered.*

*18. The process of claim 12, wherein said oxygen containing gas is oxygen, or air.*

*19. The method of claim 10, further comprising operating the refrigerant system, the refrigerant system comprising said E-1,3,3,3-tetrafluoropropene recovered.*

*20. The method of claim 1, wherein the isomeric selectivity of the 1,3,3,3-tetrafluoropropene as directly formed from the 1,1,1,3,3-pentafluoropropane is at least 99.7 mol % E-isomer.*

*21. The method of claim 11, wherein the isomeric selectivity of the 1,3,3,3-tetrafluoropropene as directly formed from the 1,1,1,3,3-pentafluoropropane is at least 99.7 mol % E-isomer.*

*22. The method of claim 1, wherein the contacting is conducted at a temperature held between 275° C. and 350° C.*

*23. The method of claim 11, wherein the contacting is conducted at a temperature held between 275° C. and 350° C.*

*24. The method of claim 1, wherein the product mixture includes a mole ratio of E-1,3,3,3-tetrafluoropropene to Z-1,3,3,3-tetrafluoropropene of about 5.7 to about 6.*

*25. The method of claim 11, wherein the product mixture includes a mole ratio of E-1,3,3,3-tetrafluoropropene to Z-1,3,3,3-tetrafluoropropene of about 5.7 to about 6.*

* * * * *